US012201790B2

(12) United States Patent
Engler et al.

(10) Patent No.: US 12,201,790 B2
(45) Date of Patent: Jan. 21, 2025

(54) TUBE SECUREMENT DEVICE

(71) Applicant: Solventum Intellectual Properties Company, Maplewood, MN (US)

(72) Inventors: Amanda C. Engler, Woodbury, MN (US); Denise J. Ziemann, Fridley, MN (US); Richard L. Jacobson, Stillwater, MN (US); Kimberly A. Schommer, Hudson, WI (US); Elizabeth A. Tatroe, Lakeland Shores, MN (US); Michael J. Turnbull, Woodbury, MN (US); Jeffrey D. Cotton, Saint Paul, MN (US); Jener De Oliveira, Sumare-Sp (BR)

(73) Assignee: Solventum Intellectual Properties Company, Maplewood, MN (US)

( * ) Notice: Subject to any disclaimer, the term of this patent is extended or adjusted under 35 U.S.C. 154(b) by 764 days.

(21) Appl. No.: 17/432,137

(22) PCT Filed: Mar. 6, 2020

(86) PCT No.: PCT/IB2020/051975
§ 371 (c)(1),
(2) Date: Aug. 19, 2021

(87) PCT Pub. No.: WO2020/183325
PCT Pub. Date: Sep. 17, 2020

(65) Prior Publication Data
US 2022/0168546 A1 Jun. 2, 2022

Related U.S. Application Data

(60) Provisional application No. 62/817,703, filed on Mar. 13, 2019.

(51) Int. Cl.
*A61M 25/02* (2006.01)
*A61J 15/00* (2006.01)
*A61M 16/04* (2006.01)

(52) U.S. Cl.
CPC .......... *A61M 25/02* (2013.01); *A61J 15/0003* (2013.01); *A61J 15/0061* (2013.01);
(Continued)

(58) Field of Classification Search
CPC .... A61F 5/08; A61F 5/30; A61F 5/56; A61M 25/02; A61M 2025/0226;
(Continued)

(56) References Cited

U.S. PATENT DOCUMENTS 4,823,789 A * 4/1989 Beisang, III .......... A61M 25/02
128/911
D827,144 S 8/2018 Oliveira
(Continued)

FOREIGN PATENT DOCUMENTS

CN 100500243 6/2009
CN 101732165 A 6/2010
(Continued)

OTHER PUBLICATIONS

International Search Report for PCT International Application No. PCT/IB2020/051975, mailed on Aug. 26, 2020, 6 pages.
(Continued)

*Primary Examiner* — Manuel A Mendez
(74) *Attorney, Agent, or Firm* — Mueting Raasch Group

(57) ABSTRACT

The disclosed tube securement device attaches to the patient's body and to the tube, while allowing for a section of the tube to be detached from the tube securement device. The tube securement device comprises a backing with adhesive coated sections. The backing comprises a first end section, a second end section, and a midsection, separating the first end section from the second end section. The tube securement device further comprises a first adhesive on at least a portion of the first major surface of the first end section, a second adhesive on at least a portion of the first
(Continued)

major surface of the second end section, and wherein the first major surface of the midsection is free of tacky adhesive.

13 Claims, 3 Drawing Sheets

(52) U.S. Cl.
CPC ... *A61M 16/0497* (2013.01); *A61M 2025/022* (2013.01); *A61M 2025/0226* (2013.01); *A61M 2025/0266* (2013.01)

(58) Field of Classification Search
CPC .... A61M 2025/0253; A61M 2025/026; A61M 2025/022; A61M 2025/0266; A61M 16/0688; A61M 16/0497; A61M 16/0666; A61M 16/0672; A61M 16/0477; A61M 16/0488; A61M 2210/0618; A61J 15/0003; A61J 15/0034; A61J 15/0061
See application file for complete search history.

(56) References Cited

U.S. PATENT DOCUMENTS

| | | | | |
|---|---|---|---|---|
| 11,013,667 | B2* | 5/2021 | Oliveira | A61J 15/0003 |
| 2009/0292256 | A1 | 11/2009 | Cubberly | |
| 2019/0076616 | A1* | 3/2019 | Walters | A61M 16/0497 |
| 2022/0339384 | A1* | 10/2022 | Cullinane | A61M 16/0688 |

FOREIGN PATENT DOCUMENTS

| | | |
|---|---|---|
| CN | 201871101 U | 6/2011 |
| CN | 204017100 U | 12/2014 |
| CN | 104398389 A | 3/2015 |
| CN | 205698801 | 11/2016 |
| EP | 1712249 | 10/2006 |
| JP | 2000339643 A | 12/2000 |
| JP | 2002253602 A | 9/2002 |
| JP | 3183192 U | 5/2023 |
| KR | 200416835 | 5/2006 |
| KR | 100858334 | 9/2008 |
| WO | WO 1997-024222 | 10/1997 |
| WO | WO 1998-032481 | 7/1998 |
| WO | WO 2016-159783 | 10/2016 |
| WO | WO 2017-034907 | 3/2017 |
| WO | WO 2017-034909 | 3/2017 |
| WO | WO 2017-034911 | 3/2017 |
| WO | WO 2017-034912 | 3/2017 |
| WO | WO 2017-034913 | 3/2017 |
| WO | 2018039584 A1 | 3/2018 |
| WO | WO 2018-160649 | 9/2018 |
| WO | WO 2020-183326 | 12/2020 |

OTHER PUBLICATIONS

International Search Report for PCT International Application No. PCT/IB2020/051977, mailed on Jul. 1, 2020, 5 pages.

* cited by examiner

TUBE SECUREMENT DEVICE

CROSS REFERENCE TO RELATED APPLICATIONS

This application is a national stage filing under 35 U.S.C. 371 of PCT/IB2020/051975, filed Mar. 6, 2020, which claims the benefit of U.S. Provisional Application No. 62/817,703, filed Mar. 13, 2019, the disclosures of which are incorporated by reference in their entirety herein.

TECHNICAL FIELD

The present disclosure relates to a tube securement device and methods of using a tube securement device.

BACKGROUND

At times, it may be necessary to insert tubes into a patient for different purposes, such as, feeding, air supply, and/or liquid removal. Such tubes generally need to be attached to the patient's skin in order to maintain the correction position of the tube.

Tubes inserted through the nose are referred to as a nasogastric (NG) tube and can be used for various applications, including feeding, drug administration and/or stomach drainage. Tubes inserted through the mouth are referred to an endotracheal tubes (ET) tubes. Tubes entering or exiting a body need to be securely attached to the patient's skin in order to maintain the correct position of the tube internally, such as inside the stomach, mouth, or airway. These tubed inside of a patient can be uncomfortable to the patient.

SUMMARY

The disclosed tube securement device securely attaches to the patient's body and to the tube, while allowing for a section of the tube to be detached from the tube securement device. When fully adhesive coated tapes are used to secure a tube to the body, all movement of the tube translates to movement of the tube, which can cause pain an irritation. In the disclosed tube securement device, the detached section of the tube from the tube securement device will allow for a small amount of tube movement.

The tube securement device comprises a backing with adhesive coated sections. The backing has a first major surface and a second major surface, opposite the first major surface. The backing comprises a first end section, a second end section, and a midsection, separating the first end section from the second end section. The first end section, second end section, and midsection extend along a longitudinal direction. The first end section is wider than the midsection in a lateral direction that is perpendicular to the longitudinal direction. The tube securement device further comprises a first adhesive on at least a portion of the first major surface of the first end section, a second adhesive on at least a portion of the first major surface of the second end section, and wherein the first major surface of the midsection is free of tacky adhesive.

In one embodiment, the backing comprises a plurality of layers. In one embodiment, the backing is selected from paper, film, woven, knitted, nonwoven, or combinations thereof.

In one embodiment, the second end section is wider than the midsection in a lateral direction that is perpendicular to the longitudinal direction. In one embodiment, the second end section is wider than the midsection in the lateral direction that is perpendicular to the longitudinal direction.

In one embodiment, the first end section is wider than the midsection in a first lateral direction that is perpendicular to the longitudinal direction symmetrical and wider than the midsection in a second lateral direction that is opposite the first lateral direction. In one embodiment, the first end is symmetrical in the first lateral direction and second lateral direction.

In one embodiment, the first adhesive and second adhesive are pressure sensitive adhesives. In one embodiment, the first adhesive and second adhesive are selective from an acrylate or a silicone adhesive. In one embodiment, the first adhesive is a silicone adhesive and second adhesive is an acrylate adhesive.

In one embodiment, the first major surface of the midsection that is free of tacky adhesive comprises one of: (i) a midsection adhesive composition detackified to form the first major surface that is free of tacky adhesive; (ii) a midsection adhesive composition covered to form the first major surface that is free of tacky adhesive, or (iii) no adhesive composition to form the first major surface that is free of tacky adhesive.

In one embodiment, a system for securing a tube to a skin or a body, such as a nose, lip, cheek, comprises a tube securement device. The tube securement device comprises a backing having a first major surface and a second major surface, opposite the first major surface, wherein the backing comprises a first end section, a second end section, and a midsection, separating the first end section from the second end section. The first end section, second end section, and midsection extend along a longitudinal direction. The first end section is wider than the midsection in a lateral direction that is perpendicular to the longitudinal direction. A first adhesive on at least a portion of the first major surface of the first end section. A second adhesive on at least a portion of the first major surface of the second end section. The first major surface of the midsection is free of tacky adhesive. The first adhesive of the first end section is secured to the body. The second adhesive of the second end section is secured to the tube. The midsection is detached from the tube.

While the above-identified drawings and figures set forth embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of this invention. The figures may not be drawn to scale.

DETAILED DESCRIPTION

Commonly, tape strips are used to wrap around a tube and secure the tubes to a patient. This can provide secure attachment of the tube to the skin, but this is also a very rigid and inflexible connection of the tube to the patient. Tubes, like NG tubes or ET tubes are uncomfortable inside the sensitive tissue of the nose and mouth, respectively. Because the very secure connection of the tube from the tape, any movements from the face or the tube will cause actuation of the tube inside the sensitive tissue of the patient.

The disclosed tube securement device secures to the patient's body, such as a nose, mouth, lip, cheek, etc., and to the tube, but includes a midsection that is detached from the tube. Therefore, this detached section of the tube from the tube securement device will allow for a small amount of tube movement relative to the tape securement device. This small amount of movement prevents every movement of the face or the tube from actuating tube against the inside of the patients body. In other words, the tube is slightly more free to suspend from the tube securement device to allow for very slight movements of the tube.

Figure 1:
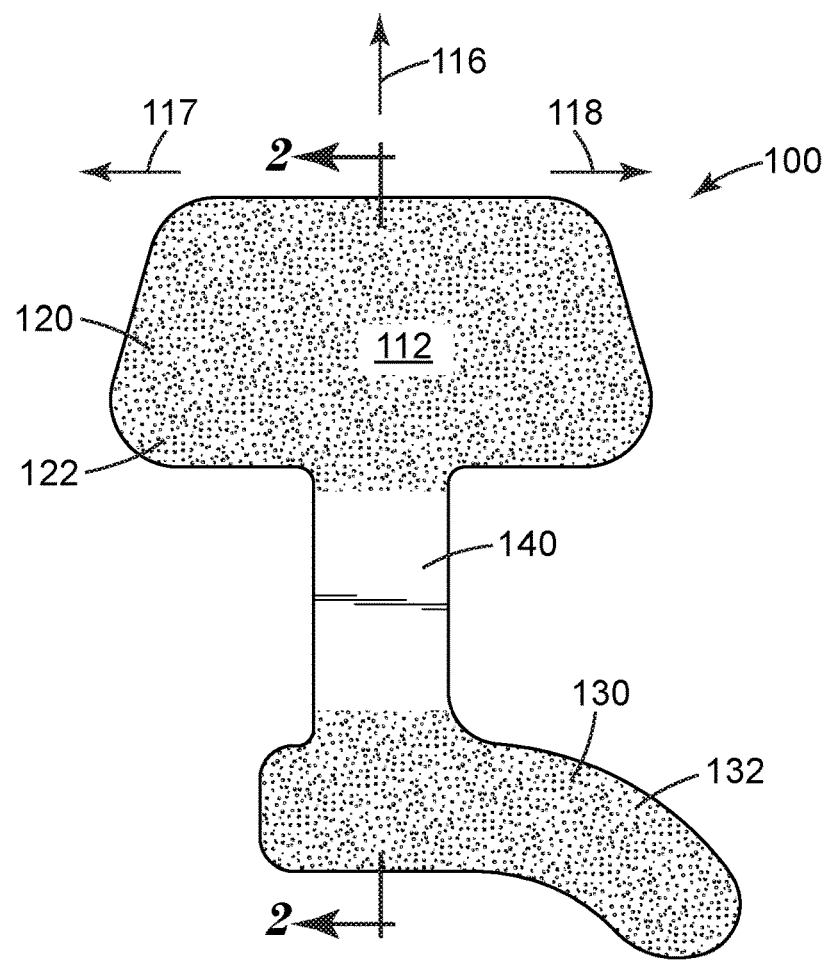
FIG. 1 is a plan view of one embodiment of a tube securement device.
Figure 2:
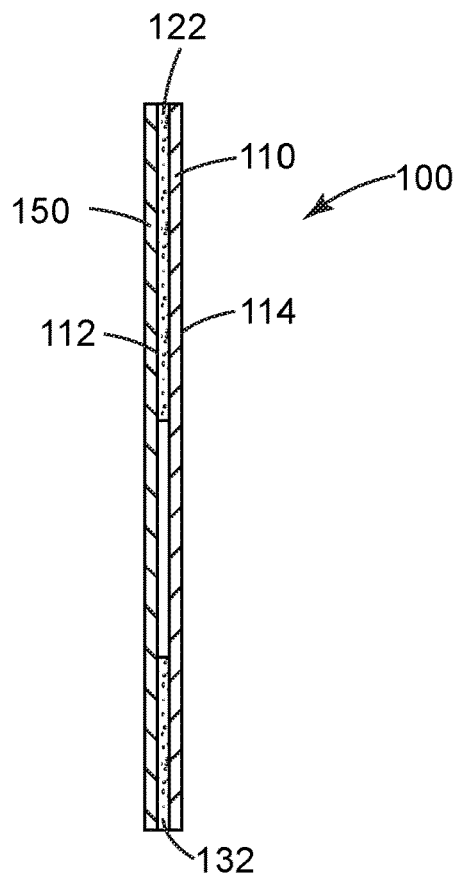
FIG. 2 is a side sectional view of the tube securement device of FIG. 1.
Figure 3:
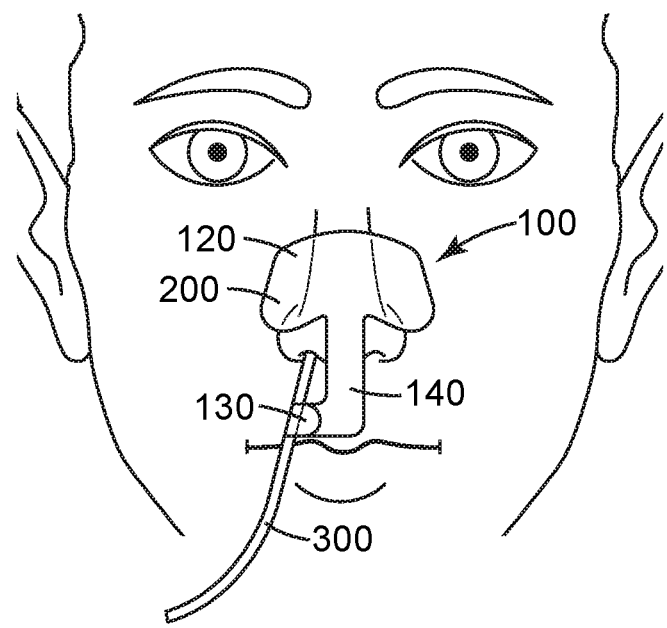
FIG. 3 is a front view of the tube securement device of FIG. 1 secured to a tube and to a person.

FIG. 1 is a plan view of one embodiment of a tube securement device 100, showing the first major surface that contains the adhesive surfaces. FIG. 2 is a side sectional view of the tube securement device 100 of FIG. 1 through line 2-2, with the addition of a release liner 150. FIG. 3 is a front view of the tube securement device 100 of FIG. 1 secured to a tube 300 and to a nose 200.

The tube securement device 100 has a first major surface 112 and a second major surface 114, opposite the first major surface 112. The first major surface 112 is shown in FIG. 1 and is the surface containing the adhesive, described below.

The tube securement device 100 comprises a backing 110. The backing 110 is made from a flexible material that will contour to the nose 200 as well as the tube 300. Common materials for the backing 110 include paper, film, woven, knitted, nonwoven materials. The backing 110 can be a single layer or a multilayer construction. The backing 110 can be formed from materials that absorb or allow for transmission of moisture vapor generated from the skin at the nose 200.

The tube securement device 100 comprises a first end section 120, a second end section 130 and a midsection 140, separating the first end section 120 from the second end section 130. Typically, the single, unitary backing material 110 material extends continuously from the first end section 120, the second end section 130 and the midsection 140, such as shown in the embodiment in FIGS. 1-2. It is understood, that the backing may comprise integrated sections that form the first end section 120, a second end section 130 and a midsection 140 such that the material forming each section is not identical to the other sections.

As shown in FIG. 1, the first end section 120, second end section 130, and midsection 140 extend along a longitudinal direction 116. In this embodiment, the first end section 120, second end section 130, and midsection 140 are linearly arranged along the longitudinal direction 116. It is understood that it is not necessary the first end section 120, second end section 130, and midsection 140 be linearly arranged, but could be offset or extend at a diagonal, for example.

The first end section 120 is wider than the midsection 140 in a lateral direction 117 that is perpendicular to the longitudinal direction 116, and much wider than the midsection 140 in a lateral direction 118. In the embodiment shown in FIGS. 1-3, the first end section 120 contacts the nose 200. Therefore, a wider portion of the first end section 120 allows for secure attachment to the nose 200, without the bulk of material overlying the tube 300 at the midsection 140. In some embodiments, see for example FIG. 5, the wider first end section 120 is the portion that contacts the tube 300. Therefore, the wider portion of the first end section 120 allows for secure attachment to the tube 300 and possibly for wrapping around the tube 300 one or more times.

Figure 4:
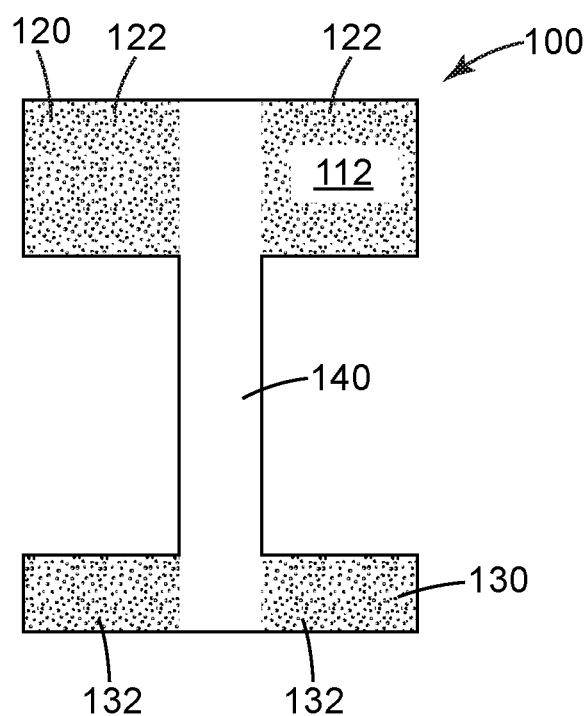
FIG. 4 is a plan view of a second embodiment of a tube securement device.

In some embodiments, like shown in FIGS. 1 and 4, the second end section 130 is wider than the midsection 140 in a lateral direction 117 that is perpendicular to the longitudinal direction 116. When the first end section 120 is used to secure to the nose, the wider portion of the second end section 130 is secured to the tube 300 and allows for secure attachment to the tube 300 and possibly for wrapping around the tube 300 one or more times.

In some embodiments, like shown in FIGS. 1 and 4, the first end section 120 is symmetrical in a first lateral direction 117 and second lateral direction 118 so that the first end section 120 can be placed centrally on the nose. It is understood that this is not required and the first end section 120 can be of any variety of shapes and sizes to secure to a body. If securing to a nose, for example, the first end section 120 may be fitted to just a single side of the nose 200 and not centrally on the nose 200.

Similarly, the second end section 130 may extend in only in a first lateral direction 117, like shown in FIG. 1 or may extend symmetrically in a first lateral direction 117 and second lateral direction 118, like shown in the embodiment of FIG. 4.

Various shapes of the tube securement device suitable for the tube securement device 100 are shown in PCT publications: WO 2017/034907, WO 2017/034909, WO 2017/034911, WO 2017/034912, WO 2017/034913, and WO 2018/160649, the disclosures of which are herein incorporated by reference.

The first major surface 112 contains the adhesive on the tube securement device 100. The adhesive is any suitable adhesive that will secure on contact to skin or secure to a tube. Such an adhesive may be referred to as having tack. For example, pressure sensitive adhesives, hydrogels, or hydrocolloids can be used.

A first adhesive 122 is on at least a portion of the first major surface 112 of the first end section 120. A second adhesive 132 is on at least a portion of the first major surface 112 of the second end section 130. As can be seen in the embodiment in FIG. 3, the first adhesive 122 at the first end section 120 secures to the nose 200, and the second adhesive 132 at the second end section 130 secures to the tube 300.

FIG. 2 shows an optional release liner 150 that covers all or a portion of the adhesives 122, 132 to prevent contamination of the adhesives 122, 132 prior to use. In one embodiment, the release liner 150 may be the package that contains the tube securement device 100. Suitable release liners can be made of papers or films, such as, for example kraft papers, polyethylene, polypropylene, polyester or composites of any of these materials. In one embodiment, the liners are coated with release agents such as fluorochemicals or silicones.

Having the first adhesive 122 and second adhesive 132 on the first major surface 112 gives at least three benefits. First, it is more efficient to apply the first adhesive 122 and second adhesive 132 to a single side of the tube securement device 100 during manufacturing. Second, for packaging the tube securement device 100, a single release liner 150, can be used to cover both the first adhesive 122 and second adhesive 132 prior to use, minimizing the total amount and cost of material in the tube securement device 100. Third, once the tube securement device 100 is applied, such as shown in FIG. 3, the first adhesive surface 122 and second adhesive surface 132 are both facing the patient and therefore are less likely to interfere with the nurse or doctor's hands during application.

In some embodiments, second end section 130 is entirely covered with the second adhesive 132, such as shown in FIG. 1. In some embodiment, a portion of the second end section 130, typically at the perimeter edge, is free of second adhesive 132, to function as a tab to allow for easy removal of the second end section 130 from the tubing.

The first or second adhesive 122, 132 can include any adhesive that provides acceptable adhesion to skin and is acceptable for use on skin (e.g., the adhesive should preferably be non-irritating and non-sensitizing). Suitable adhesives are pressure-sensitive and in certain embodiments have a relatively high moisture vapor transmission rate to allow for moisture evaporation. Suitable adhesives include those based on acrylates, urethane, hydrogels, hydrocolloids, block copolymers, silicones, rubber based adhesives (including natural rubber, polyisoprene, polyisobutylene, butyl rubber etc.) as well as combinations of these adhesives. The adhesive component may contain tackifiers, plasticizers, rheology modifiers, absorbent particles or fibers as well as active components including for example an antimicrobial agent.

The first adhesive 122 and second adhesive 132 may be compositionally the same adhesive. For example, both the first adhesive 122 and second adhesive 132 may be acrylate pressure sensitive adhesives or silicone pressure sensitive adhesives. In other embodiments, the first adhesive 122 and second adhesive 132 are different from one another. It may be desirable to use one adhesive that is well suited for securing to skin, while a different adhesive is used that is suited for securing to tubing.

The first major surface 112 of the midsection 140 is free of tacky adhesive. This means that the first major surface 112 of the midsection 140 will not secure on contact with skin or tubing. There are various ways of providing the first major surface 112 of the midsection 140 that is free of tacky adhesive. In one embodiment, such as shown in FIG. 2, at the midsection 140 no adhesive composition is applied at the first major surface 112 of the midsection and therefore the first major surface 112 is free of tacky adhesive.

In another embodiment, if the midsection 140 is covered with an adhesive composition, then the adhesive could be detackified so that the first major surface 112 is free of tacky adhesive. Adhesives can be detackified by using commonly know techniques, such as, for example, radiation curing or applying coatings.

In another example, if the midsection 140 is covered with an adhesive composition, then the adhesive composition could be covered to form the first major surface 112 that is free of tacky adhesive. The covering could be a film, paper, or other non-tacky material. Regardless of how it is formed, the midsection includes a first major surface 112 that is free of tacky adhesive.

In use, the first adhesive 122 of the first end section 120 secures to the body, such as the nose 200, the second adhesive 132 of the second end section 130 secures to the tube 300, and the midsection 140, which is free of tacky adhesive. As can be seen in FIG. 3, the midsection 140 is not in direct contact with the tube 300. In use, the tube securement device 100 secures to the patient's body, such as a nose 200, and to the tube 300, like shown in FIG. 3. Because the midsection 140 is free of tacky adhesive, the midsection 140 is detached from the tube. The result is that the tube securement device 100 allows the tube 300 to be suspended from first end section 120. Therefore, this detached section of the tube 300 from the tube securement device 100 will allow for a small amount of tube 300 movement relative to the tape securement device 100.

To use the tube securement device 100, the release liner 150 (if provided) is removed to expose the first adhesive 122 and second adhesive 132. Then, first adhesive 122 is secured to the body, such as the nose 300. Then the second adhesive 132 is secured to the tube 300. During application, the first major surface 112, containing the first adhesive 122 and second adhesive 132 is facing the body.

As shown in FIG. 3, the first end section 120 with the first adhesive 122 is secured to the nose 200. The second end section 130 with the second adhesive 132 secures to the tube 300 and is able to wrap around the tube. The midsection 140 is adjacent to the tube 300 but is not directly secured to the tube 300. The tube securement device 100 securely attached the tube 300 to the body, but not such a rigid securement that all movement of the tube 300 forces the tube 300 against the inner surface of the nose.

FIG. 4 is a plan view of a second embodiment of a tube securement device 100 showing the first major surface 112 containing the adhesive. Reference numbers in FIG. 4 identify the corresponding features as shown in FIG. 1. In this embodiment in FIG. 4, the first adhesive 122 and second adhesive 132 are applied in a pattern on the first major surface 112. Therefore, there are portions of the first end section 120 and second end section 130 that are free of tacky adhesive. Limiting the adhesive coverage can increase the moisture vapor permeability through the backing.

Additionally, in this embodiment in FIG. 4, the second end section 130 extend in both a first lateral direction 117 and second lateral direction 118 wider than the midsection 140 providing more coverage for securing to the tube 300.

Figure 5:
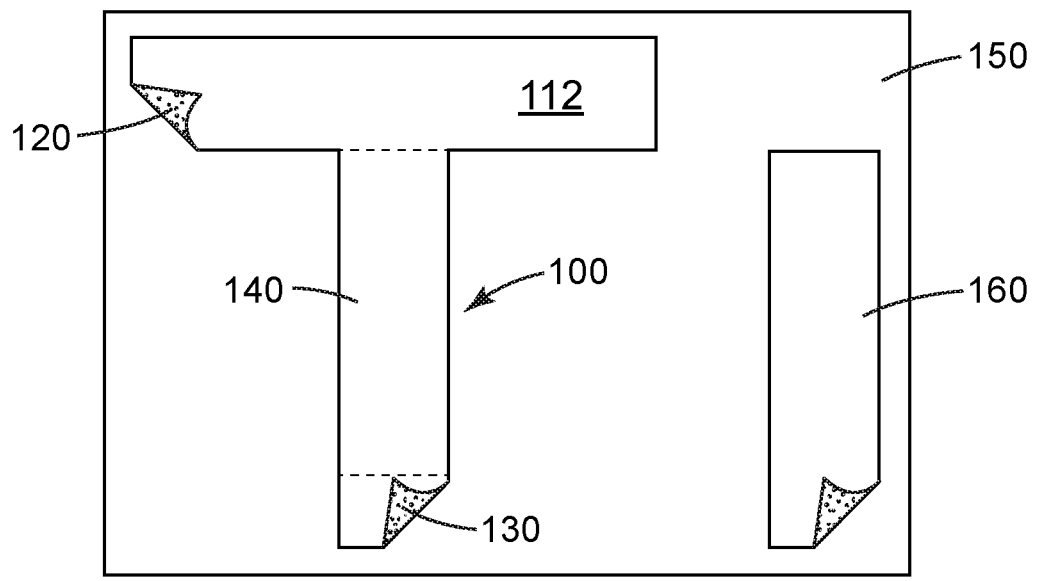
FIG. 5 is a plan view of a third embodiment of a tube securement device.

FIG. 5 is a plan view of a third embodiment of a tube securement device 100 showing a release liner 150 that the first major surface 112 containing the adhesive is secured to. Therefore, the tube securement device 100 is shown slightly peeled up from the release liner 150. The dotted line is intended to show the break in the area with adhesive and the area of the midsection without the tacky adhesive. Reference numbers in FIG. 5 identify the corresponding features as shown in FIG. 1. In this embodiment, only the first end section 120 is wider than the midsection 140 in a lateral direction 117, while the second end section 130 is of the same width as the midsection 140. Additionally, in this embodiment in FIG. 5, the first adhesive 122 and second adhesive 132 are applied in a pattern on the first major surface 112. First end section 120 or section end section 130 could be used to apply to the body, such as a nose.

Figure 6:
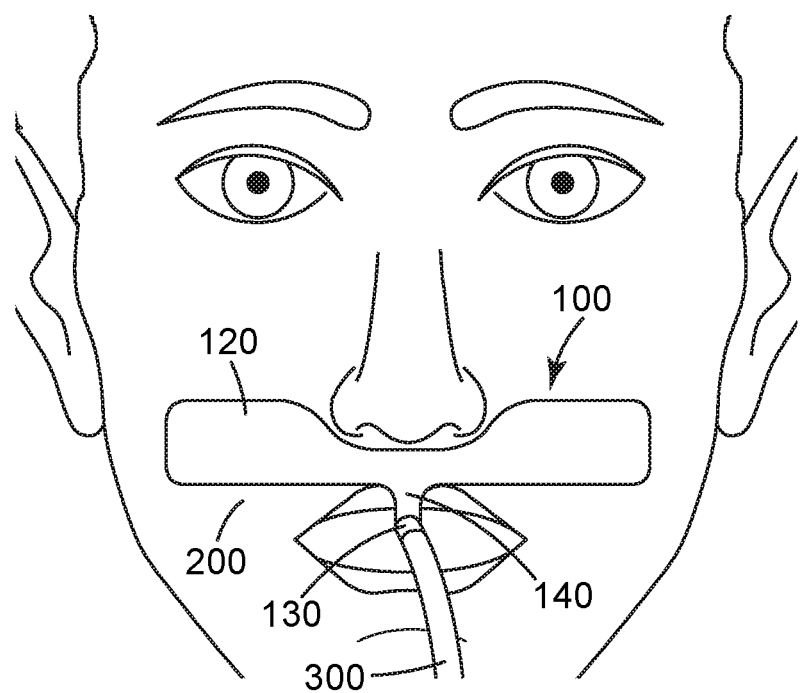
FIG. 6 is a front view of a fourth embodiment of a tube securement device secured to a tube and to a person.

FIG. 6 is a front view of a third embodiment of a tube securement device 100 secured to a lip 200 and to a tube 300. In this embodiment the tube 200 is an endotracheal tube. Reference numbers in FIG. 6 identify the corresponding features as shown in FIG. 1. In this embodiment in FIG. 6, the tube securement device 100 include a first end section 120 with first adhesive (not apparent in this figure) secured to the body 200 at the upper lip and second end section 130 with second adhesive (not apparent in this figure) secured to the tube 300. Between the first end section 120 and second end section 130 is the midsection 140, that is free of tacky adhesive. The first end section 120 includes a recess for improving the fit in the narrow section between the nose and lip, so that larger sections of the first end section 120 can provide more contact area at the face. In this embodiment, the midsection 140 is relative short compared to the midsection 140 shown in FIGS. 1-5 for less flexibility and less translation of the ET tube. To use the tube securement device 100, the first end section 120 is secured to the body, such as the upper lip and cheeks, and the second end section 130 is secured to the tube 300.

The tube securement devices 100 disclosed herein can be manufactured using commonly used film converting, coating, cutting, and packaging techniques. For example, in one embodiment, the backing 110 is coated with the first adhesive 122 and second adhesive. Then, the coated backing is cut to the shape of the tube securement device 100. A release liner 150 may be applied to entire first major surface 112 of the tube securement device.

In some embodiments, like shown in FIG. 5, the release liner 150 is overall larger in size than the tube securement device 100. The excess release liner 150 aids in peeling the tube securement device 100 from the release liner 150. Additional components, such as an adhesive tape strip 160, can also be secured to the excess release liner 150.

Although specific embodiments have been shown and described herein, it is understood that these embodiments are merely illustrative of the many possible specific arrangements that can be devised in application of the principles of the invention. Numerous and varied other arrangements can be devised in accordance with these principles by those of skill in the art without departing from the spirit and scope of the invention. The scope of the present invention should not be limited to the structures described in this application, but only by the structures described by the language of the claims and the equivalents of those structures.

What is claimed is:

1. A tube securement device for securing a tube to a nose comprising:
    a backing having a first major surface and a second major surface, opposite the first major surface, wherein the backing comprises a first end section, a second end section, and a midsection, separating the first end section from the second end section;
        wherein the first end section, second end section, and midsection extend along a longitudinal direction;
        wherein the first end section is wider than the midsection in a lateral direction that is perpendicular to the longitudinal direction;
    a first adhesive on at least a portion of the first major surface of the first end section;
    a second adhesive on at least a portion of the first major surface of the second end section;
    wherein the first major surface of the midsection is free of tacky adhesive;
    wherein, in use, the first adhesive secures directly to the nose;
    wherein, in use, the second adhesive secures to the tube.

2. The tube securement device of claim 1, wherein the backing comprises a plurality of layers.

3. The tube securement device of claim 1, wherein the second end section is wider than the midsection in a first lateral direction that is perpendicular to the longitudinal direction.

4. The tube securement device of claim 1, wherein the first end is symmetrical about an axis that is parallel to the longitudinal direction.

5. The tube securement device of claim 1, wherein the first adhesive and second adhesive are selective from an acrylate or a silicone adhesive.

6. The tube securement device of claim 1, wherein the first adhesive is a silicone adhesive and second adhesive is an acrylate adhesive.

7. The tube securement device of claim 1, wherein the first major surface of the midsection that is free of tacky adhesive comprises a midsection adhesive composition detackified to form the first major surface that is free of tacky adhesive.

8. The tube securement device of claim 7, wherein the first adhesive, second adhesive, and midsection adhesive composition are of the same material and continuously along the entire first major surface.

9. The tube securement device of claim 1, wherein the first major surface of the midsection that is free of tacky adhesive comprises a midsection adhesive composition covered to form the first major surface that is free of tacky adhesive.

10. The tube securement device of claim 9, wherein the first adhesive, second adhesive, and midsection adhesive composition are of the same material and continuously along the entire first major surface.

11. The tube securement device of claim 1, wherein the first major surface of the midsection that is free of tacky adhesive comprises (ii) or (iii) no adhesive composition to form the first major surface that is free of tacky adhesive.

12. A tube securement device for securing a tube to a nose comprising:
    a backing having a first major surface and a second major surface, opposite the first major surface, wherein the backing comprises a first end section, a second end section, and a midsection, separating the first end section from the second end section;
        wherein the first end section, second end section, and midsection extend along a longitudinal direction;
        wherein the first end section is wider than the midsection in a lateral direction that is perpendicular to the longitudinal direction;
    an adhesive on the first major surface at the first end section, second end section, and midsection;
    a cover over the a midsection adhesive, such that the first major surface of the midsection is free of tacky adhesive;
    wherein, in use, the adhesive at the first end section secures directly to the nose;
    wherein, in use, the adhesive at the second end section secures to the tube.

13. A tube securement device for securing a tube to a nose comprising:
    a backing having a first major surface and a second major surface, opposite the first major surface, wherein the backing comprises a first end section, a second end section, and a midsection, separating the first end section from the second end section;
        wherein the first end section, second end section, and midsection extend along a longitudinal direction;
        wherein the first end section is wider than the midsection in a lateral direction that is perpendicular to the longitudinal direction;
    an adhesive on the first major surface at the first end section, second end section, and midsection;
    wherein the adhesive at the midsection is detackified, such that the first major surface of the midsection is free of tacky adhesive;
    wherein, in use, the adhesive at the first end section secures directly to the nose;
    wherein, in use, the adhesive at the second end section secures to the tube.

* * * * *